(12) United States Patent
Qing et al.

(10) Patent No.: US 8,347,722 B2
(45) Date of Patent: Jan. 8, 2013

(54) METHOD AND APPARATUS FOR CONDUCTING STRUCTURAL HEALTH MONITORING IN A CRYOGENIC, HIGH VIBRATION ENVIRONMENT

(75) Inventors: Xinlin Qing, Cupertino, CA (US); Shawn J. Beard, Livermore, CA (US); Irene Li, Stanford, CA (US)

(73) Assignee: Acellent Technologies, Inc., Sunnyvale, CA (US)

( * ) Notice: Subject to any disclaimer, the term of this patent is extended or adjusted under 35 U.S.C. 154(b) by 762 days.

(21) Appl. No.: 12/358,108

(22) Filed: Jan. 22, 2009

(65) Prior Publication Data

US 2009/0217761 A1     Sep. 3, 2009

Related U.S. Application Data

(60) Provisional application No. 61/022,761, filed on Jan. 22, 2008.

(51) Int. Cl.
*G01N 29/14* (2006.01)
(52) U.S. Cl. ............................ 73/587; 73/632
(58) Field of Classification Search .................. 73/587, 73/597, 632, 788, 801, 804; 702/85, 116
See application file for complete search history.

(56) References Cited

U.S. PATENT DOCUMENTS

| | | | | |
|---|---|---|---|---|
| 3,924,456 | A * | 12/1975 | Vahaviolos | 73/770 |
| 4,126,033 | A * | 11/1978 | Bartoli et al. | 374/44 |
| 6,006,163 | A * | 12/1999 | Lichtenwalner et al. | 702/36 |
| 6,370,964 | B1 * | 4/2002 | Chang et al. | 73/862.046 |
| 6,491,095 | B2 * | 12/2002 | Kompanek | 166/249 |
| 6,799,466 | B2 * | 10/2004 | Chinn | 73/622 |
| 7,487,059 | B2 * | 2/2009 | Davis et al. | 702/116 |
| 7,589,457 | B2 * | 9/2009 | Lee et al. | 310/338 |
| 7,590,510 | B2 * | 9/2009 | Kim | 702/183 |
| 7,596,078 | B2 * | 9/2009 | Beard et al. | 370/201 |
| 7,743,659 | B2 * | 6/2010 | Kearns et al. | 73/632 |

* cited by examiner

*Primary Examiner* — J M Saint Surin
(74) *Attorney, Agent, or Firm* — Innovation Counsel LLP (57) ABSTRACT

Sensors affixed to various such structures, where the sensors can withstand, remain affixed, and operate while undergoing both cryogenic temperatures and high vibrations. In particular, piezoelectric single crystal transducers are utilized, and these sensors are coupled to the structure via a low temperature, heat cured epoxy. This allows the transducers to monitor the structure while the engine is operating, even despite the harsh operating conditions. Aspects of the invention thus allow for real time monitoring and analysis of structures that operate in conditions that previously did not permit such analysis. A further aspect of the invention relates to use of piezoelectric single crystal transducers. In particular, use of such transducers allows the same elements to be used as both sensors and actuators.

17 Claims, 6 Drawing Sheets

METHOD AND APPARATUS FOR CONDUCTING STRUCTURAL HEALTH MONITORING IN A CRYOGENIC, HIGH VIBRATION ENVIRONMENT

This application claims the benefit of U.S. Provisional Application No. 61/022,761, filed on Jan. 22, 2008, the entire content of which is hereby incorporated by reference.

GOVERNMENT RIGHTS

The U.S. Government has a paid-up license in this invention and the right in limited circumstances to require the patent owner to license others on reasonable terms as provided for by the terms of Contract No. NNM06AA19C awarded by NASA.

BRIEF DESCRIPTION OF THE INVENTION

This invention relates generally to structural health monitoring. More specifically, this invention relates to conducting structural health monitoring in a cryogenic, high vibration environment.

BACKGROUND OF THE INVENTION

Structural health monitoring seeks to determine the health of structures, typically by employing sensors/actuators distributed upon a structure. Actuators commonly query the structure, and sensors detect these querying signals, whereupon the detected signals are analyzed to determine whether any defects (e.g. cracks, pits, delaminations, etc.) or signs of failure have developed. It is often desired that these monitoring systems be capable of operating in a nondestructive manner (i.e. that the systems be capable of monitoring structures without causing any damage to them), and operating while the structure itself is undergoing normal operations.

However, such nondestructive monitoring is challenging when the structure operates in, or generates, an extreme environment. For example, the monitoring of structures such as liquid propellant rocket engines is often desired, as high operating stresses make devastating and dangerous structural failures more likely. However, these structures also generate harsh operating conditions that pose great challenges to implementation of monitoring systems. In particular, monitoring systems must be able to simultaneously withstand both cryogenic temperatures (typically, the temperatures at which liquid propellant such as liquid oxygen or liquid hydrogen is stored) and the high vibrations generated by engine operation. Accordingly, it is desirable to develop structural health monitoring systems capable of operating in cryogenic, high vibration environments.

Furthermore, the harsh conditions presented during operation prevent sensors from being repositioned while the structure is in use. This limits many conventional monitoring systems to a fixed configuration in which only certain portions of the structure can be monitored, in only certain ways. It is therefore also desirable to develop structural health monitoring systems capable of operating in cryogenic, high vibration environments in a flexible and adaptive manner, so as to be able to detect and assess structural failures and other problems at different locations in real time, without need for repositioning sensors.

SUMMARY OF THE INVENTION

The invention can be implemented in a number of ways, including as a system and as a method.

In one embodiment, a system for performing structural health monitoring in a cryogenic, high vibration environment comprises a plurality of piezoelectric single crystal transducers affixed to a structure with a cryogenic adhesive, each transducer of the plurality of piezoelectric single crystal transducers configured to transmit stress waves through the structure at a monitoring frequency and to detect stress waves at the monitoring frequency and at a structural vibration frequency. The system also includes a signal filter in electrical communication with the plurality of piezoelectric single crystal transducers, the signal filter configured to substantially pass signals at the monitoring frequency and to substantially attenuate signals at the structural vibration frequency.

In another embodiment, a system for performing structural health monitoring of a structure in a cryogenic, high vibration environment comprises a plurality of piezoelectric single crystal transducers affixed to a structure with a cryogenic adhesive, and an analysis unit electrically connected to and positioned remotely from the plurality of piezoelectric single crystal transducers. The analysis unit comprises a signal transmission module configured to transmit electrical signals to the plurality of piezoelectric single crystal transducers, wherein the electrical signals are first signals transmitted at a monitoring frequency. The analysis unit also includes a signal filter in electrical communication with the plurality of piezoelectric single crystal transducers and configured to receive second and third signals from the plurality of piezoelectric single crystal transducers, the second signals corresponding to signals detected from the first signals, and the third signals corresponding to structural vibration occurring at a structural vibration frequency. The signal filter is configured to substantially pass ones of the second signals at the monitoring frequency and to substantially attenuate ones of the third signals.

In another embodiment, a method of monitoring the health of a structure in a cryogenic, high vibration environment comprises receiving signals from one or more sensors, the signals corresponding to vibrations of a structure having a cryogenic temperature, the vibrations including a first vibration and a second vibration, wherein the first vibration is an operational vibration and the second vibration is a monitoring signal. The method also includes filtering the received signals so as to attenuate ones of the signals corresponding to the first vibration and so as to pass ones of the signals corresponding to the second vibration. Then, the presence of a defect in the structure is determined according to the passed ones of the signals.

Other aspects and advantages of the invention will become apparent from the following detailed description taken in conjunction with the accompanying drawings which illustrate, by way of example, the principles of the invention.

BRIEF DESCRIPTION OF THE DRAWINGS

For a better understanding of the invention, reference should be made to the following detailed description taken in conjunction with the accompanying drawings, in which.

Like reference numerals refer to corresponding parts throughout the drawings.

DETAILED DESCRIPTION OF EMBODIMENTS OF THE INVENTION

One aspect of the invention is a structural health monitoring system capable of operating in a cryogenic, high vibration environment such as that produced by a liquid propellant rocket engine. Structures within such engines (e.g., fuel lines, pumps, etc.) are often exposed to cryogenic temperatures and, when the engine is firing, very high vibrations. Thus, one exemplary monitoring system employs sensors affixed to such structures, where the sensors can withstand, remain affixed, and operate while undergoing both cryogenic temperatures and high vibrations. In particular, piezoelectric single crystal transducers are utilized, and these sensors are coupled to the structure via a low temperature, heat cured epoxy. This allows the transducers to monitor the structure while the engine is operating, even despite the harsh operating conditions. Aspects of the invention thus allow for real time monitoring and analysis of structures that operate in conditions that previously did not permit such analysis.

A further aspect of the invention relates to use of piezoelectric single crystal transducers. In particular, use of such transducers allows the same elements to be used as both sensors and actuators. Accordingly, given transducers can be utilized repeatedly either as sensors or actuators, in various combinations. This allows the monitoring system to query various different sensor paths without repositioning the transducers, in turn allowing the system to detect and assess problems at different locations in real time.

Figure 1A:
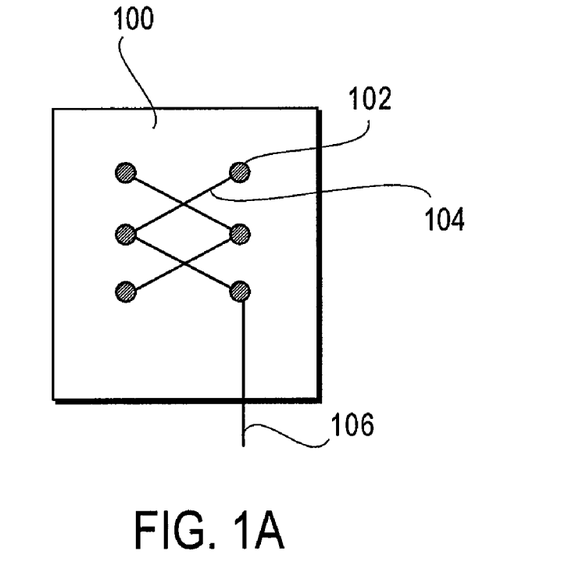
FIG. 1A illustrates a top view of a sensing layer manufactured in accordance with embodiments of the present invention.

FIG. 1A illustrates a flexible sensing layer for use in accordance with embodiments of the present invention. A diagnostic layer 100 is shown, which contains an array of sensors 102. The sensors 102 can be sensors capable of receiving signals used in structural health monitoring such as stress waves, and are connected to conductive traces 104. The traces 104 connect (or interconnect, if necessary) sensors 102 to one or more output leads 106 configured for connection to a processor or other device capable of analyzing the data derived from the sensors 102.

The diagnostic layer 100 and its operation are further described in U.S. Pat. No. 6,370,964 to Chang et al., which is hereby incorporated by reference in its entirety and for all purposes. Construction of the diagnostic layer 100 is also explained in U.S. Pat. No. 7,413,919 to Qing et al., which is also incorporated by reference in its entirety and for all purposes. It should be noted that the present invention is not limited to the embodiments disclosed in the aforementioned U.S. Pat. No. 7,413,919, but instead encompasses the use of flexible sensor layers having any configuration. For illustration, FIG. 1B further describes aspects of the operation of the diagnostic layer 100. In operation, the output leads 106 are electrically connected to an analysis unit such as an analyzer 108, suitable for analyzing signals from the sensors 102.

Figure 1B:
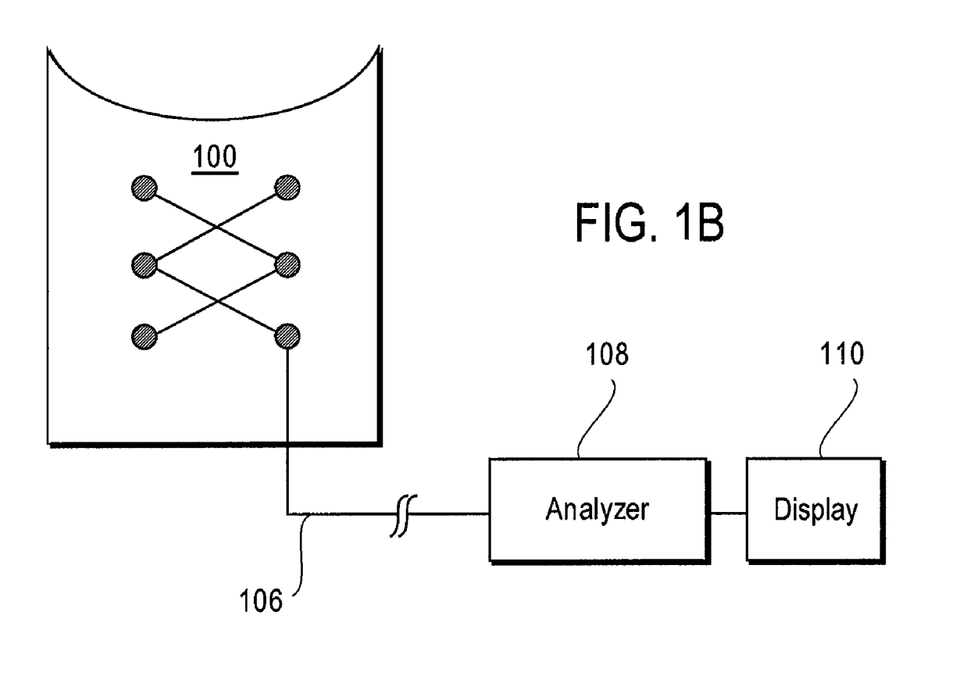
FIG. 1B illustrates a block diagram of a structural health monitoring system employing the sensing layer of FIG. 1A.

In certain embodiments, the flexible layer 100 is first attached to a structure in a manner that allows the sensing elements 102 to detect quantities related to the health of the structure. For instance, the sensors 102 can be sensors configured to detect stress waves propagated within the structure, and emit electrical signals accordingly. The analyzer 108 then analyzes these electrical signals in known manner, to assess various aspects of the health of the structure. For instance, detected stress waves can be analyzed to detect crack propagation within the structure, delamination within composite structures, or the likelihood of fatigue-related failure. Quantities such as these can then be displayed to the user via display 110. In other embodiments, the sensing elements 102 can be directly bonded or affixed to the structure.

As noted above, structures such as liquid propellant rocket engines present their associated sensing elements 102 with cryogenic, high vibration environments. For example, many components of the engines are maintained at cryogenic temperatures, commonly as cold as −252° C. for engines using liquid hydrogen, or −218° C. for engines using liquid oxygen. Conducting structural health monitoring during engine operation thus requires sensing elements 102 to be able to withstand, and operate while undergoing, both temperature and vibration extremes. This is accomplished by affixing the sensing elements 102 (and/or the flexible layer 100) to the structure with a low temperature adhesive. It has been found that the adhesive EP29LPSP from Master Bond® is a suitable adhesive. EP29LPSP is a two component, heat cured epoxy that is capable of adhering through cryogenic temperatures and high vibrations. However, it should be noted that, while EP29LPSP is a suitable adhesive and may be preferred for various applications, the invention is not limited to this specific adhesive. Instead, the invention contemplates use of any adhesive capable of bonding sensing elements to a structure in a manner that can withstand both cryogenic temperatures and high vibrations, while still allowing sensors to monitor the structure.

Figure 2:
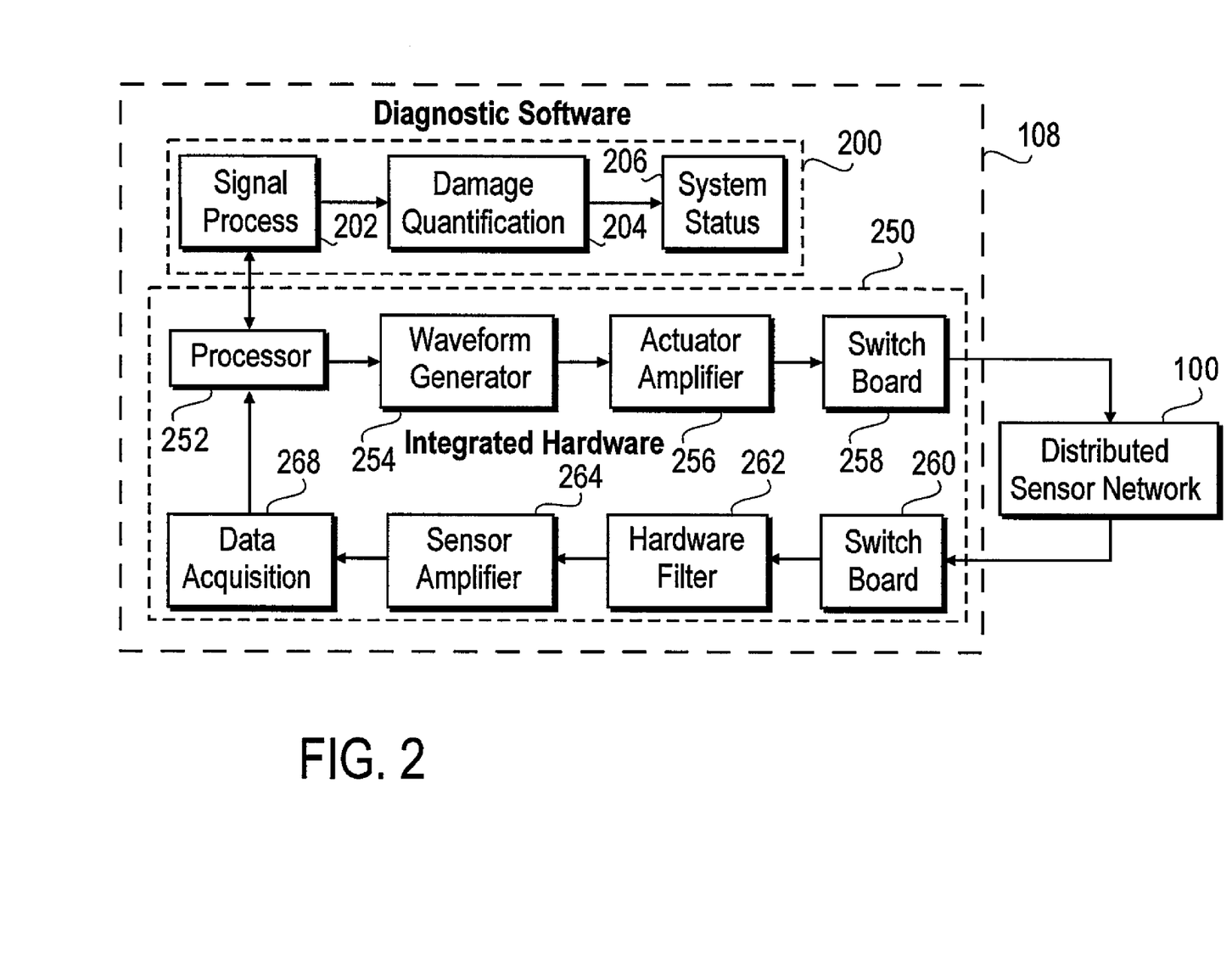
FIG. 2 is a block diagram illustrating further details of an exemplary analysis unit for use with structural health monitoring systems of the present invention.

FIG. 2 is a block diagram illustrating further details of the analyzer 108. The analyzer 108 includes a software module 200 and a hardware module 250. The software module 200 includes a signal processing sub-module 202, a damage quantification sub-module 204, and system status sub-module 206. The hardware module 250 includes a processor 252, waveform generator 254, actuator amplifier 256, and first switch board 258, each of which are used in transmitting monitoring signals to the sensors 102. The hardware module 250 also includes a second switch board 260, hardware filter 262, sensor amplifier 264, and data acquisition module 268, each of which can be employed in processing detected signals from the sensors 102.

The processor 252 can be a conventional processor configured to execute instructions from the software modules 202-206, and direct the waveform generator 254 to generate monitoring signal waveforms. The actuator amplifier 256 amplifies the monitoring signals generated by the waveform generator 254, while the first switch board 258 switches individual sensors 102 on/off at the direction of processor 252, to direct the monitoring signals along the appropriate sensor paths. In this manner, monitoring signals are sent to appropriate sensors 102, which in turn generate diagnostic stress waves within the structure.

Others of the sensors 102, in particular those switched on by the second switch board 260, detect these stress waves and convert them to electrical signals that are transmitted to the switch board 260, then on to the hardware filter 262.

At this point, it should be noted that operation of structures such as rocket engines typically generates large vibrations. In the case of liquid fuel rocket engines, these vibrations are commonly about 3 kHz or less. Embodiments of the invention accordingly utilize monitoring signals that are higher in frequency, such as approximately 300 kHz or more. The filter 262 is a high pass filter configured to pass signal frequencies in the range of the frequencies of the monitoring signals, and configured to attenuate signal frequencies in the range of the frequencies at which the monitored structures, e.g. rocket engines, typically vibrate during operation. It should be noted that the invention contemplates use of any appropriate filter, constructed in any manner, which attenuates frequencies in the range of operating frequencies of the structure and passes frequencies in the range of structural health monitoring signals.

Filtered signals are sent to the sensor amplifier 264 where they are sufficiently amplified for use by the data acquisition module 268. The data acquisition module 268 records/stores signals for processing by the processor 252. The processor 252 processes the signals according to the various software modules. In particular, the signal processing sub-module 202, damage quantification sub-module 204, and system status sub-module 206 process the signals and analyze them to determine the extent of any structural damage. The invention contemplates any form of software module 200 sufficient to execute monitoring of a structure.

Figure 3A:
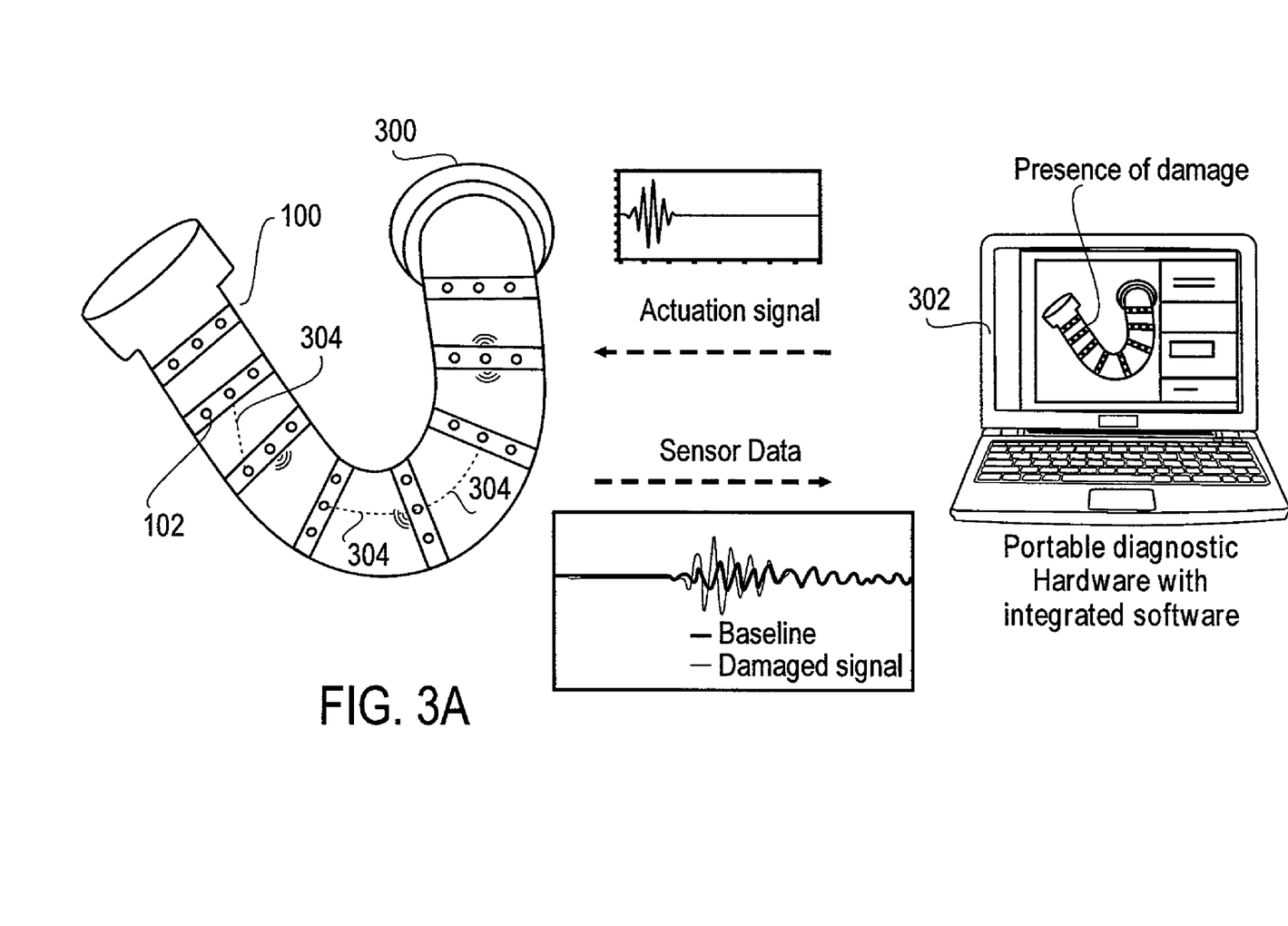
FIG. 3A conceptually illustrates operation of structural health monitoring systems of the present invention.

FIG. 3A conceptually illustrates operation of the system described above. Here, pipe 300 is an element of a liquid propellant rocket engine, and carries liquid at cryogenic temperatures (e.g., liquid oxygen/hydrogen propellant, coolant, etc.). During engine operation, the pipe 300 is also subjected to high vibration. Flexible substrates 100 are affixed to pipe 300 with a low temperature adhesive such as EP29LPSP, or alternatively, transducers 102 are bonded directly to pipe 300 with such an adhesive. Computer 302 (i.e., analyzer 108) contains hardware and software for querying any number of sensor paths 304 by sending actuation signals to transducers along any path 304, receiving sensor data back from transducers at the other end of that path 304, and analyzing/displaying the data. The transducers 102 are piezoelectric single crystal transducers capable of operating in a cryogenic environment.

In operation, baseline signals for each sensor path 304 are first collected and stored in computer 302, so that the baseline state of the pipe 300 is known. The invention contemplates any manner of baseline signal storage and collection.

Once baseline signals are stored, the pipe 300 can then be monitored. At any time, the computer 302 can transmit actuation signals to any transducer 102, inducing it to send corresponding stress waves through the pipe 300. These stress waves are detected by transducers 102 at the opposite ends of sensor paths 304, where they are converted to data signals and sent back as sensor data to computer 302. The transducers 102 convert detected stress waves, i.e. vibrations, to electrical signals. These signals are then sent to computer 302 as sensor data.

As the sensors 102 detect both stress waves resulting from monitoring signals (i.e., sent from other transducers 102) and those resulting from vibrations caused by engine operation, the sensor data contains components corresponding to the monitoring signals, as well as other components corresponding to structure vibration. If monitoring signal frequencies are chosen so as to be in a frequency range that does not overlap with the range of structural vibration frequencies, data components corresponding to structural vibration can be filtered out via filter 262. In the present embodiment, rocket engine operational vibration frequencies are commonly in the range of 3 kHz or less, and monitoring signal frequencies can be set at 300 kHz or more. The filter 262 can thus be configured accordingly, to substantially attenuate the lower-frequency engine vibration components and pass the higher-frequency monitoring signal components.

The invention contemplates any type of filter, hardware or software. Additionally, while the present embodiment is discussed in the context of a rocket engine with lower operational vibration frequencies than those of the monitoring signals, the invention encompasses any structures having any vibration frequencies, and any monitoring signal frequencies, so long as the monitoring signals are capable of being isolated and analyzed. Thus, the invention contemplates use of high pass, low pass, band pass, and any other type of filter that can be used to isolate monitoring signal frequencies.

If the structural properties of the pipe 300 have not changed along those paths 304, the sensor data will reflect an undamaged pipe 300. Conversely, if the structural properties of the pipe 300 have changed along those paths, e.g. if the pipe has developed a crack or sustained some other type of damage intersecting those paths 304, the damage will alter any stress waves that intersect it, indicating damage. Damage can be detected in any manner, but in the case of stored baseline signals, a comparison can be made between the baseline data for paths 304 and the new sensor data collected for those same paths. If the new data varies from the baseline data to a sufficient degree, such as shown by the bottom graph of FIG. 3A, it can be deemed that damage has occurred along those paths.

As above, the substrates 100 and transducers 102 are bonded to pipe 300 with an adhesive capable of withstanding a cryogenic, low temperature environment. Thus, embodiments of the invention allow for monitoring and damage detection in pipe 300, even though the pipe 300 presents an extremely hostile environment during its operation. Additionally, as the transducers 102 are separated from the computer 302 by leads 106, the computer 302 can be located remote from the pipe 300, in a less-hostile environment. Embodiments of the invention thus have the advantage of allowing for real time monitoring of structures in harsh environments where many conventional monitoring methods, such as manual inspection, would be impractical or impossible.

It should be noted that the use of transducers 102, rather than elements that can act as only sensors or only actuators, confers additional advantages. In particular, because any element 102 can function as both a sensor and as an actuator, many different sensor paths 304 can be scanned without moving any transducer 102. That is, a single sensor network can scan and analyze multiple different sensor paths 304, and even adaptively change the layout of those sensor paths 304 monitored, during rocket operation. Thus, embodiments of the invention allow for scanning of multiple different, and even changing, paths 304 even in a harsh environment when manually moving a sensor is difficult or impossible.

Those of ordinary skill in the art will realize that the above described analysis methods are simply exemplary, and that the invention contemplates a structural health monitoring system or systems capable of monitoring cryogenic, high vibration structures according to any method. For example, the hardware filter 262 can be implemented as any frequency filter, and can even be omitted, such as when a software filter is preferred. Any suitable signals can be employed as monitoring signals, for instance a five peak modulated sine wave or any other. Baseline signals can be stored and utilized for damage detection in any manner, such as comparison of the peak magnitudes of received and baseline signals, average magnitudes, or any other suitable approach. In addition, while they are desirable in many applications, the invention contemplates embodiments in which baseline signals need not be employed.

Figure 3B:
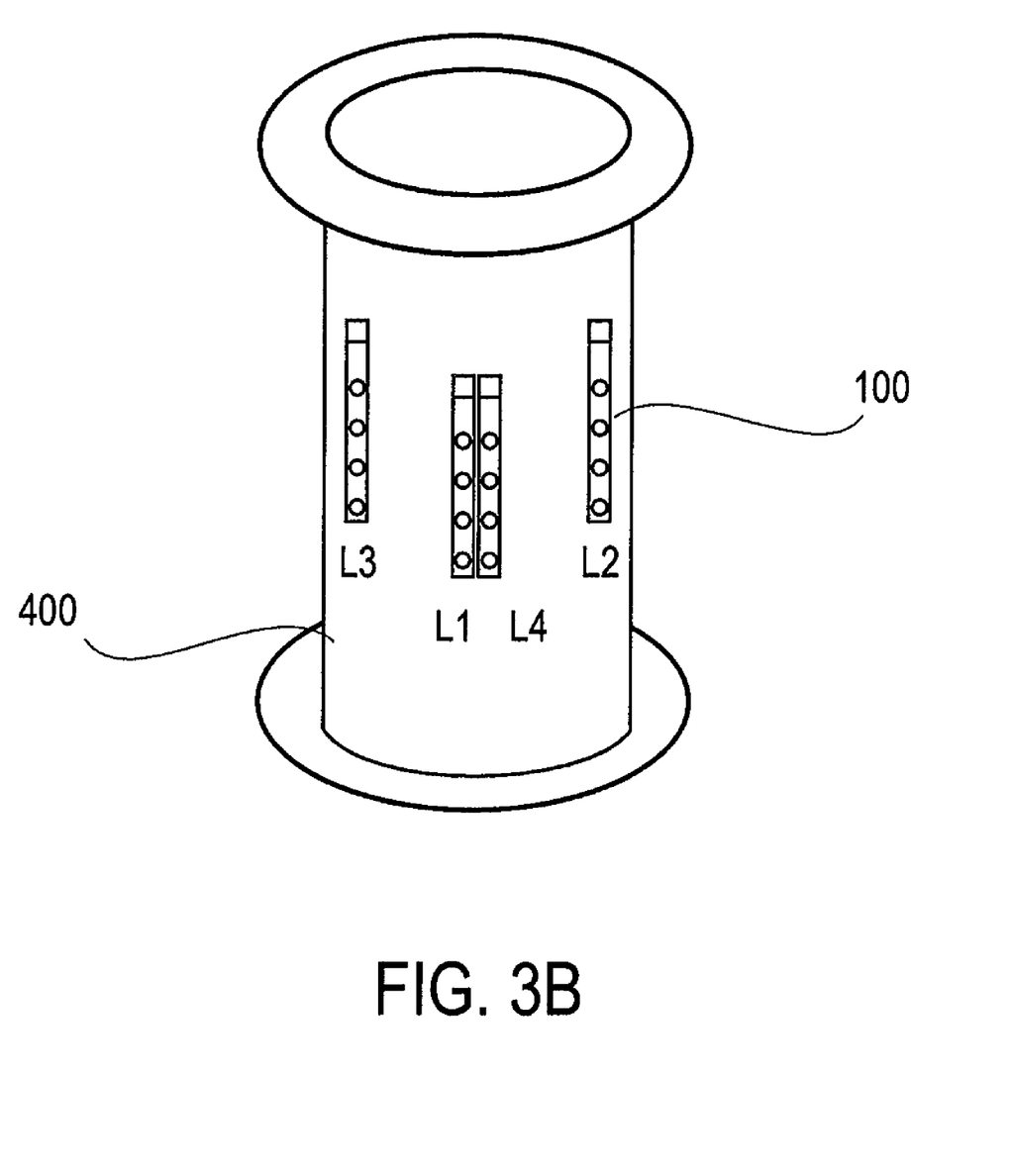
FIG. 3B illustrates exemplary placement of transducers on a cryogenic, high vibration structure.

The invention also contemplates the ability to analyze almost any structure, by placement of transducers 102 and/or substrates 100 in any location suitable for monitoring. FIG. 3B illustrates one such sensor placement scheme. Here, substrates 100 are placed in pairs L1/L3 and L2/L4, forming sensor paths between each of transducers in these pairs. More specifically, a sensor path exists between each pair of transducers in substrates L1 and L3, and also between each pair of transducers in substrates L2 and L4. This allows each area A, B to be scanned independently by any pair of transducers in, respectively, substrate pairs L1/L3 and L2/L4.

Aspects of the invention have been verified by testing. In particular, tests have confirmed that transducers, substrates, and adhesives encompassed by the invention effectively withstand the vibrations induced by rocket engine operation, as well as the cryogenic temperatures present. Testing has also confirmed the efficacy of frequency filters encompassed by the invention, as well as systems' ability to detect defects. For the following FIGS. 4A-5B, substrates L1-L4 containing piezoelectric single crystal transducers were bonded to an aluminum duct as shown in FIG. 3B. The duct was affixed to a shaker machine to simulate rocket engine vibration levels, and liquid nitrogen (LN2) was pumped through the duct. The vibration was controlled via an arithmetic average between accelerometers (not shown) on each end of the duct. The test environment was derived from operational measurements on large booster LOX-$H_2$ engines during engine hot-fire testing. In particular, the defined random and sine environments utilized represent an average of data from the large propellant duct of that booster, where the data averaged is data from the highest overall detected vibration level.

Figure 4A:
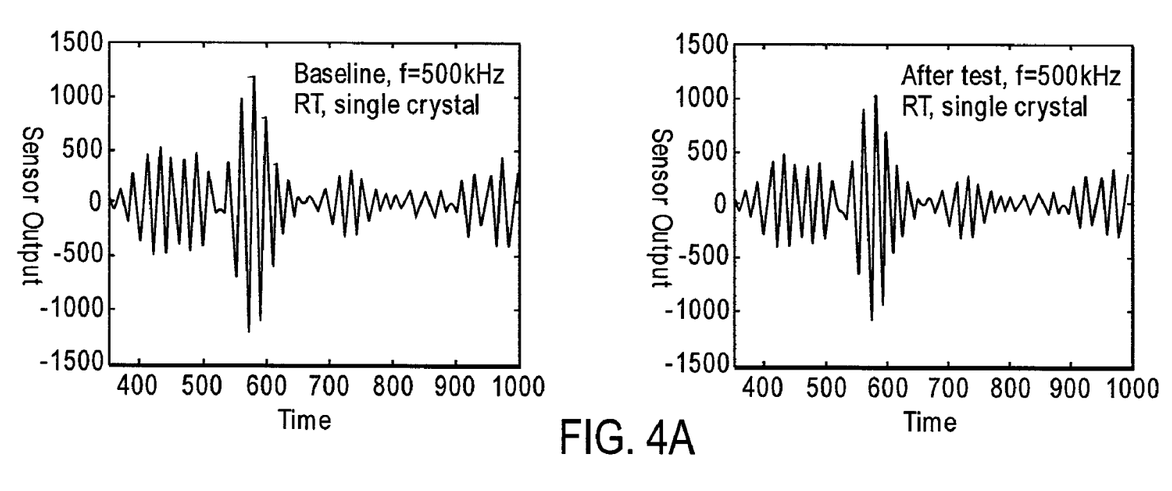
FIG. 4A is a graph of test results verifying the ability of transducers of embodiments of the invention to withstand rocket engine vibrations.
Figure 4B:
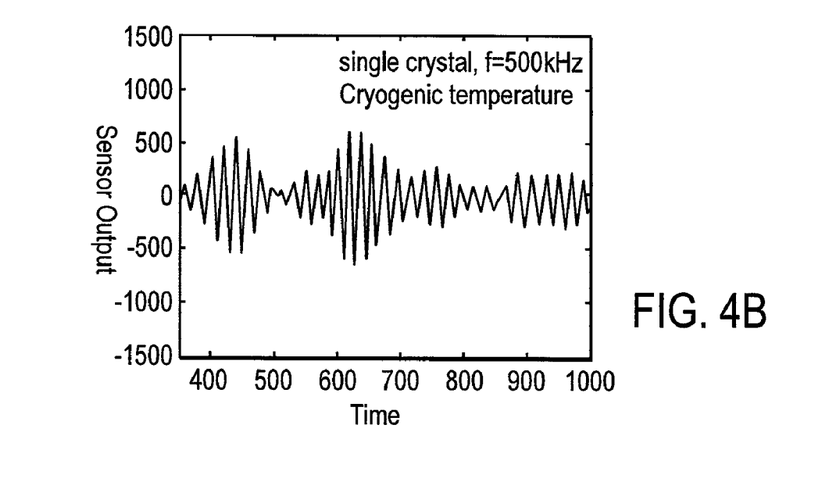
FIG. 4B is a graph of test results verifying the ability of transducers of embodiments of the invention to withstand cryogenic temperatures.

FIG. 4A shows graphs summarizing vibration test results. The left-hand graph shows an output of sensors on the duct before the sensors were subjected to simulated engine vibration levels, while the right-hand graph shows the output of those same sensors after vibration. As can be seen, the two graphs are nearly identical, confirming that transducers and adhesives of the invention can withstand, and function during, the vibration levels that exist during operation of a liquid rocket engine.

FIG. 4A is a graph summarizing temperature test results. The graph shows signals output from the transducers (again, piezoelectric single crystal transducers affixed to the duct via EP29LPSP) while the duct assembly was chilled down to cryogenic temperatures, with no external vibration applied (i.e., the signals detected are stress waves from monitoring signals sent by another transducer; no simulated rocket engine vibration was applied to the test structure). As can be seen, the signals output from a piezoelectric single crystal transducer at cryogenic temperature are largely the same as those produced by piezoelectric single crystal transducers room temperature, and are certainly of sufficient quality to perform almost any structural health monitoring analyses.

Figure 5A:
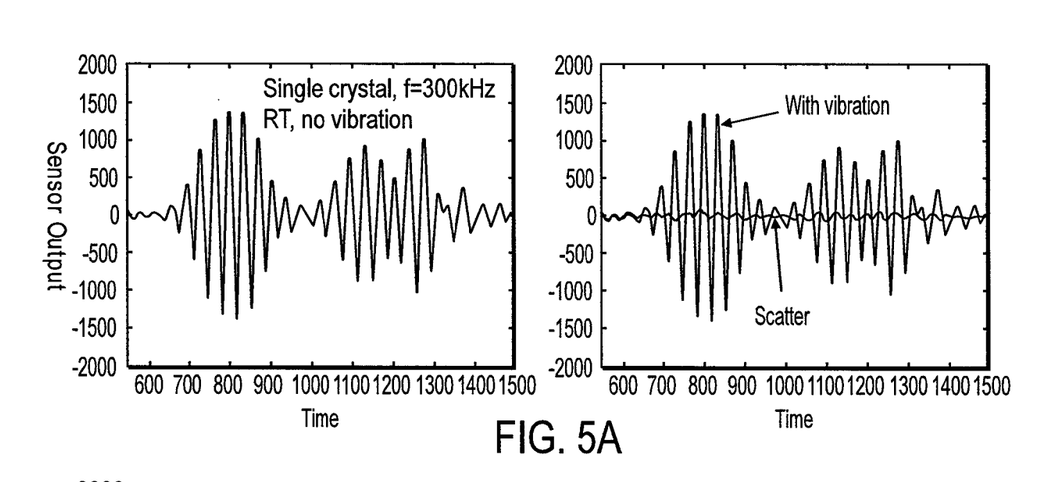
FIG. 5A is a graph of test results verifying the effectiveness of frequency filters of embodiments of the invention.

FIG. 5A shows graphs summarizing the efficacy of a frequency filter. The left-hand graph shows sensor output of a detected monitoring signal without external vibration (i.e., simulated rocket engine operational vibrations) applied, indicating that the sensor properly detected the monitoring signal. The right-hand graph shows the output of that same sensor, detecting the same monitoring signal, with external vibration applied, and after a frequency filter is used to filter out the external vibration. From the right-hand graph, it can be seen that a hardware filter effectively attenuates signals due to external vibration, isolating the monitoring signals for analysis. Scatter signals are delayed in time and of significantly lower magnitude, and thus are not of concern.

Figure 5B:
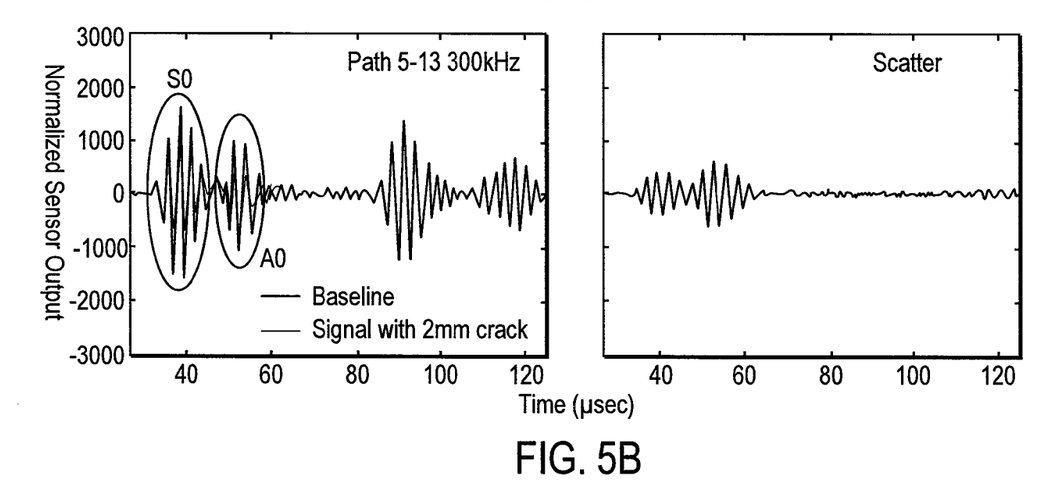
FIG. 5B is a graph of test results verifying the ability of embodiments of the invention to detect structural defects.

FIG. 5B shows graphs summarizing the effectiveness of the tested embodiment in detecting defects. In particular, the left-hand graph shows superimposed signals recorded from test sensors before and after a 2 mm crack was introduced in the duct, along the sensor path. As can be seen, the crack produces a clear change in both the S0 and A0 modes, indicating that damage can be readily detected by embodiments of the invention. As with FIG. 5A, it can also be seen that scatter signals are delayed in time and of significantly lower magnitude, and thus are not of concern.

The foregoing description, for purposes of explanation, used specific nomenclature to provide a thorough understanding of the invention. However, it will be apparent to one skilled in the art that the specific details are not required in order to practice the invention. In other instances, well known devices are shown in block form in order to avoid unnecessary distraction from the underlying invention. Thus, the foregoing descriptions of specific embodiments of the present invention are presented for purposes of illustration and description. They are not intended to be exhaustive or to limit the invention to the precise forms disclosed. Rather, many modifications and variations are possible in view of the above teachings. For example, transducers can be placed in any arrangement and number suitable for monitoring of a structure, and any monitoring methods and suitable analysis hardware/software may be employed. The embodiments were chosen and described in order to best explain the principles of the invention and its practical applications, to thereby enable others skilled in the art to best utilize the invention and various embodiments with various modifications as are suited to the particular use contemplated. It is intended that the scope of the invention be defined by the following claims and their equivalents.

What is claimed is:

1. A system for performing structural health monitoring in a cryogenic, high vibration environment, comprising:
   a plurality of piezoelectric single crystal transducers affixed to a structure with a cryogenic adhesive, each transducer of the plurality of piezoelectric single crystal transducers configured to transmit stress waves through the structure at a monitoring frequency and to detect stress waves at the monitoring frequency and at a structural vibration frequency;
   a signal filter in electrical communication with the plurality of piezoelectric single crystal transducers, the signal filter configured to substantially pass signals at the monitoring frequency and to substantially attenuate signals at the structural vibration frequency.

2. The system of claim 1, further comprising a flexible substrate, wherein the piezoelectric single crystal transducers are each affixed to the flexible substrate, and wherein the cryogenic adhesive bonds the flexible substrate to the structure.

3. The system of claim 1, wherein the cryogenic adhesive is a low temperature, heat cured epoxy.

4. The system of claim 1, wherein the structural vibration frequency is equal to or less than approximately 3 kHz.

5. The system of claim 1, wherein the monitoring frequency is about 300 kHz or more.

6. A system for performing structural health monitoring of a structure in a cryogenic, high vibration environment, comprising:
   a plurality of piezoelectric single crystal transducers affixed to a structure with a cryogenic adhesive; and an analysis unit electrically connected to and positioned remotely from the plurality of piezoelectric single crystal transducers, the analysis unit comprising:
- a signal transmission module configured to transmit electrical signals to the plurality of piezoelectric single crystal transducers, wherein the electrical signals are first signals transmitted at a monitoring frequency; and
- a signal filter in electrical communication with the plurality of piezoelectric single crystal transducers and configured to receive second and third signals from the plurality of piezoelectric single crystal transducers, the second signals corresponding to signals detected from the first signals, and the third signals corresponding to structural vibration occurring at a structural vibration frequency;

wherein the signal filter is configured to substantially pass ones of the second signals at the monitoring frequency and to substantially attenuate ones of the third signals.

7. The system of claim 6, further comprising a flexible substrate, wherein the piezoelectric single crystal transducers are each affixed to the flexible substrate, and wherein the cryogenic adhesive bonds the flexible substrate to the structure.

8. The system of claim 6, wherein the cryogenic adhesive is a low temperature, heat cured epoxy.

9. The system of claim 6, wherein the structural vibration frequency is equal to or less than approximately 3 kHz.

10. The system of claim 6, wherein the monitoring frequency is about 300 kHz or more.

11. A method of monitoring the health of a structure in a cryogenic, high vibration environment, the method comprising:
- receiving signals from one or more sensors, the signals corresponding to vibrations of a structure having a cryogenic temperature, the vibrations including a first vibration and a second vibration, wherein the first vibration is an operational vibration and the second vibration is a monitoring signal;
- filtering the received signals so as to attenuate ones of the signals corresponding to the first vibration and so as to pass ones of the signals corresponding to the second vibration; and
- determining the presence of a defect in the structure according to the passed ones of the signals.

12. The method of claim 11, further comprising transmitting signals to one or more actuators coupled to the structure and maintained at the cryogenic temperature, so as to generate the second vibration in the structure.

13. The method of claim 12, wherein the sensors and the actuators are piezoelectric single crystal transducers.

14. The method of claim 11, further comprising coupling the sensors to the structure with a cryogenic adhesive.

15. The method of claim 14, wherein the coupling further comprises coupling the sensors to the structure with a low temperature, heat cured epoxy.

16. The method of claim 11, wherein the first vibration is equal to or less than approximately 3 kHz.

17. The method of claim 11, wherein the second vibration is about 300 kHz or more.

* * * * *